(12) United States Patent
Regan et al.

(10) Patent No.: US 6,395,554 B1
(45) Date of Patent: May 28, 2002

(54) MICROARRAY LOADING/UNLOADING SYSTEM

(75) Inventors: Donald T. Regan, Boxborough; Robert T. Milkowski, Groton; George Gyorke, Jr., Sommerville; Paul L. St. Cyr, Middleton; Sean R. Doane, Shrewsbury, all of MA (US)

(73) Assignee: Packard Instrument Company, Meriden, CT (US)

( * ) Notice: Subject to any disclaimer, the term of this patent is extended or adjusted under 35 U.S.C. 154(b) by 0 days.

(21) Appl. No.: 09/390,013

(22) Filed: Sep. 3, 1999

(51) Int. Cl.[7] .................. G01N 35/00; G01N 35/02
(52) U.S. Cl. .............. 436/46; 436/48; 422/65; 422/67; 435/289.1
(58) Field of Search .............. 422/65, 67; 435/289.1; 436/46, 48

(56) References Cited

U.S. PATENT DOCUMENTS

| | | | |
|---|---|---|---|
| 3,851,972 A | 12/1974 | Smith et al. ............. 356/72 |
| 4,367,915 A | 1/1983 | Georges ................... 350/530 |
| 4,453,807 A | 6/1984 | Faulkner et al. .......... 350/529 |
| 4,815,055 A | * 3/1989 | Fago, Jr. ................. 369/36 |
| 4,871,290 A | 10/1989 | Kaczynski et al. ........ 414/331 |
| 5,573,950 A | 11/1996 | Graessle et al. ......... 435/287.3 |
| 5,674,454 A | * 10/1997 | Karl et al. ............... 422/63 |
| 5,690,892 A | 11/1997 | Babler et al. ............. 422/63 |
| 5,871,696 A | * 2/1999 | Roberts et al. ........... 422/65 |

* cited by examiner

Primary Examiner—Nina Bhat
(74) Attorney, Agent, or Firm—Cesari and McKenna, LLP (57) ABSTRACT

A method and apparatus for a slide loading/unloading system is described. A slide storage cassette is provided to store slides in which the slides are stored with an end protruding from the slide storage cassette. A slide feeder is described having grippers, which grip the end of a slide and transport the slide to a sample holder. The sample holder receives and retains the transported slide.

45 Claims, 6 Drawing Sheets

MICROARRAY LOADING/UNLOADING SYSTEM

FIELD OF THE INVENTION

The present invention relates to an apparatus and method for use in a slide loading/unloading system and in particular, to a microarray loading/unloading system.

BACKGROUND

Deoxyribonucleic acid (DNA), ribonucleic acid (RNA) and proteins are complex molecules that are integral to every living organism. DNA contains information required to define a structure and process of a cell. RNA transfers that information by becoming a template for protein synthesis and enabling protein synthesis process. Proteins initiate and control all functions within a cell. Because of the fundamental nature of these molecules to biology, researchers have developed methods of experimenting and characterizing their structure. One method that is commonly used is called "hybridization".

Hybridization takes advantage of the complimentary nature of RNA and DNA to characterize their sequence. Typically, a reference strand of DNA (the "target") is bound to a substrate. One or more types of DNA under test (the "probes") are labeled with either radioactive or fluorescence tags. The probes are then mixed with the target. Probe molecules with a sequence similar that of to the target will bind or hybridize to the target molecules. Dissimilar probe molecules will not bind and be washed away in a subsequent rinsing process. By measuring the quantity of bound probe molecules, a researcher can determine the likeness between the probe and target. This method is used to measure a variety of biological characteristics including gene expression, genotype, and gene sequence.

Hybridization experiments are normally conducted in large quantities in order to be generally useful. There are approximately 100,000 genes in the human genome, several thousand of which are considered in a typical study. Technologies to allow for massive parallel hybridization experiments have been developed.

One such technology is the microarray. A microarray is a substrate, typically a one-by-three inch glass slide, that is "spotted" with an array of reference target genes, typically in the form of DNA. Several thousand to several tens of thousands of genes (or partial genes) in the order of 100–114 microns in diameter are generally spotted onto a typical microarray. This allows a researcher to compare the probe DNA to many targets simultaneously. The result is the ability to characterize the gene profile of a tissue or cell type under a specified condition.

Spotting is accomplished by using an instrument called an "arrayer". A typical arrayer is a robot that can spot 40 to 100 microarrays in an automated fashion. Arrayers are usually kept in an environment in which humidity is controlled, since it affects the rate of evaporation of the solution to be spotted. This is particularly important where there is significant evaporation before the solution is transferred to the substrate. Cleanliness will directly affect the quality of any microarray because the information gleaned from the microarray is the image captured at the surface of the substrate. Any artifact, such as dust or fingerprints, will degrade the fidelity of the microarray. Thus, microarrays are manually loaded into and removed from the arrayer which may affect the quality of the spotted microarray.

The next step of the microarray process is to introduce the probe DNA. The DNA is mixed in a buffer solution to enable its transfer. A small amount of probe solution is placed on the surface of the microarray. A thin piece of glass is then used to sandwich the probe with the microarray causing the probe to spread across the region that contains the target. The probes are typically labeled with fluorescence tags. The fluors convert incident light, referred to as "excitation light", into fluoresced light, referred to as "emitted light". However, the fluors are generally susceptible to damage caused by ambient light and thus, such light should be avoided. Excitation caused by ambient light degrades the efficiency of fluors prior to scanning with an imager. This damage is called photobleaching.

Next, the target and probe are hybridized. This is accomplished by putting the microarray into a humid, thermally controlled environment where it is "baked". During this stage, the target and probe molecules with similar structures bind. After hybridization, the thin piece of glass is removed and the microarray is rinsed to wash away the non-binding probe DNA. At this point, the microarray is susceptible to damage from dirt, heat and light. Image degradation caused by contamination from handling continues to be a problem. Heat can cause the probe and target to become disassociated. Further, the fluorescent labels on the probe DNA are susceptible to photobleaching.

Finally, the microarray is imaged. The substrate is loaded into an microarray imager which excites the fluors and senses the emitted light. The resulting image is analyzed to determine the density of probe DNA that hybridized to each target DNA spot. This information is used to characterize the state and structure of the probe DNA. Any dirt or marks will contribute to fluorescence which is not related to DNA density. As a result, these artifacts will reduce the accuracy of the calculations.

After the process is complete, the microarrays are often saved for later inspection. They need to be properly stored if they are to be useful in later imaging.

If the procedure above is performed manually, the procedure will be costly and time consuming. A researcher or technician is required to handle each microarray at every step in the process. The imaging process is particularly labor intensive. Each slide is inserted by hand for single slide imaging while the user waits to load the next slide. The problem becomes acute for high volume users. Research facilities that process several hundred microarrays a day will need to hire several technicians just to keep up with the imaging.

There is a further problem with tracking microarrays. In a typical lab there are many avenues of research being pursued simultaneously by separate research groups. Since the microarrays are identical to the naked eye, they are difficult to sort manually. Even if they are labeled for tracking, the large number of microarrays being used will result in some confusion and errors during the process.

As described above, microarrays are prone to damage each time that they are handled. Everything ranging from dust to fingerprints cause image artifacts that pollute the final result. Statistically, when a large number of microarrays are processed, the amount of degradation will be proportional to the amount of handling of each slide.

Microarrays are susceptible to damage if they are not stored properly. Everything from dust to light can affect the data that is gleaned from the microarray.

There are automated microarray scanning systems available currently. These systems, however require the substrate to be placed in a metal "sub-frame" or "clip" prior to loading it into the storage mechanism. Both the substrate and frame are then located into the scanning field and subsequently scanned. This approach is forgiving of dimensional variability in substrates. Further, it provides for metal-on-metal wear surfaces, which provide for a more tolerant system design. However, as throughput demands increase, the sub-frame approach becomes limiting.

Typically, high-throughput microarray applications process batches of microarrays numbering from 10 to 100, and this is increasing. Sub-frames are less attractive to the user because of the added manual labor placing each microarray into a sub-frame. Additionally, the user needs to gather sufficient sub-frames to process a batch of microarrays. Sub-frames also increase the amount of space required by each microarray in a storage mechanism and may make a system built to handle 100 or more microarrays unmanageable to use.

Downstream microarray quantitation processes require that microarray be accurately placed in a scanning field repeatedly. Sub-frames have been shown to be inadequate in this respect.

SUMMARY

In accordance with the invention, a slide storage cassette stores a plurality of slides, with an end of each slide protruding from the cassette. A slide feeder having grippers grips the end of a slide and transports the slide to a sample holder. The sample holder receives and retains the transported slide wherein one or more functions are performed on the slide. The slides are held in the cassette without the frames, thereby eliminating the problems associated with frames.

BRIEF DESCRIPTION OF THE DRAWINGS

The invention description below refers to the accompanying drawings, of which.

DETAILED DESCRIPTION

While the invention has been conceived with the loading and unloading of microarray slides in mind, the invention may be adapted for use in other areas. For example, one area of such usage may be microscopic slides. In the passages to follow, specific embodiments of the invention will be described. The specific embodiments are given to aid in the understanding of the invention and thus, should not be construed as limitations to the invention.

Figure 1:
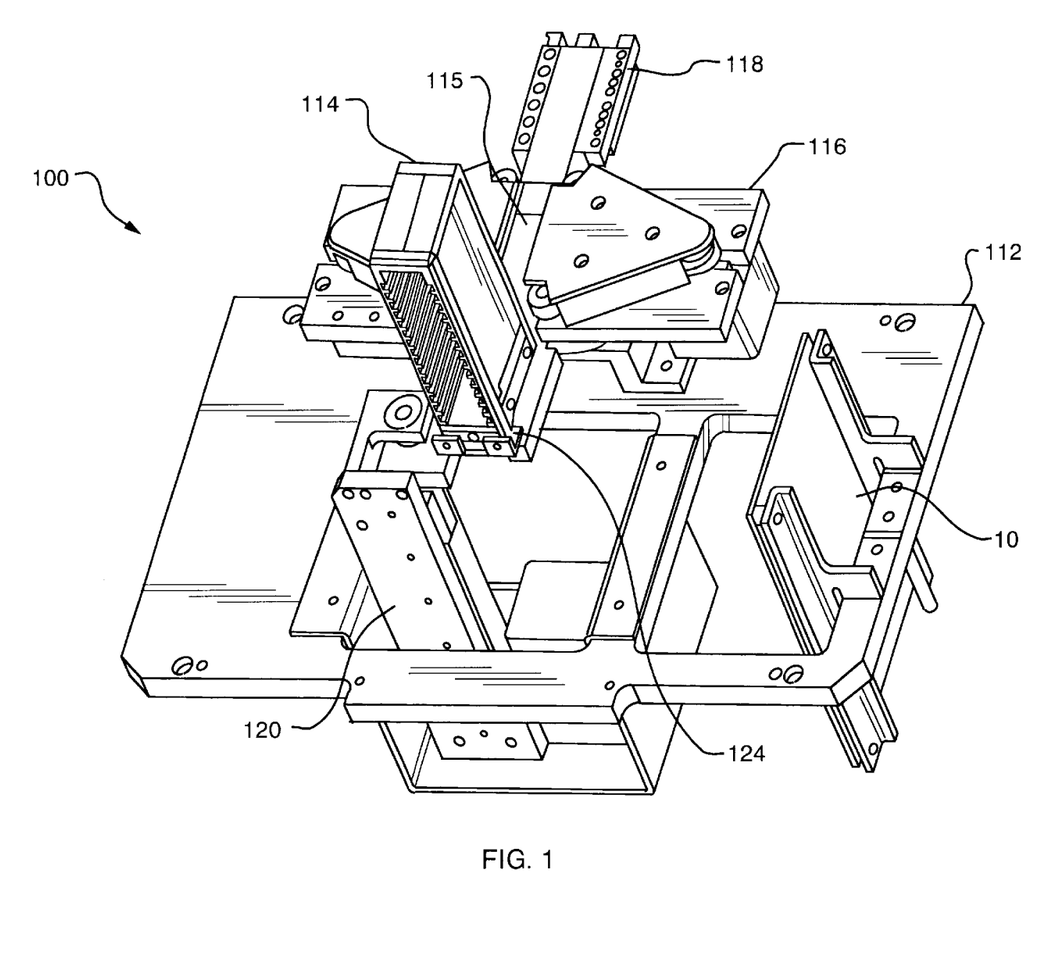
FIG. 1 is an overview of an exemplary microarray slide loading/unloading system in accordance with an embodiment of the invention.

As shown in FIG. 1, a microarray slide loading/unloading system 100 in accordance with an embodiment of the invention comprises a slide storage cassette 114 containing slides 115, a slide feeder 116, a sample holder 118 and an elevator 120.

The slides 115 are inserted into the cassette 114 with one end protruding towards the slide feeder 116. The elevator 120 moves the cassette 114 up and down until a selected slide is aligned with the slider feeder 116. Once the selected slide 115 is aligned, the slide feeder 116 grips the protruding end and transports the slide 115 to the sample holder 118. As will be further described, the slide feeder 116 is configured to compensate for the width discrepancies of the slide 115. The sample holder 118 receives and retains the slide 115. Within the sample holder 118, there are precision reference surfaces that precisely positions the slide 115. The slide 115 is subjected to one or more functions in accordance with a designed instrumentation. For example, the instrument may be a microarray scanner, a microarray spotter, a microarray hybridizer, a microarray washer, a microarray probe processing instrument and so forth.

Once the desired functions have been performed on the retained slide 115, a reverse operation similar to that described above is performed. The slide feeder 116 grips an end of the retained slide 115 from the sample holder 118 and transports the slide 115 back to the cassette 114. Once the slide is received by the cassette 114, the elevator 120 is activated to align another slide with the slide feeder 116 to repeat the process.

The cassette 114 is detachable from the elevator 120. A latch 124 located at the elevator 120 latches the cassette 114 to the elevator.

Figure 2:
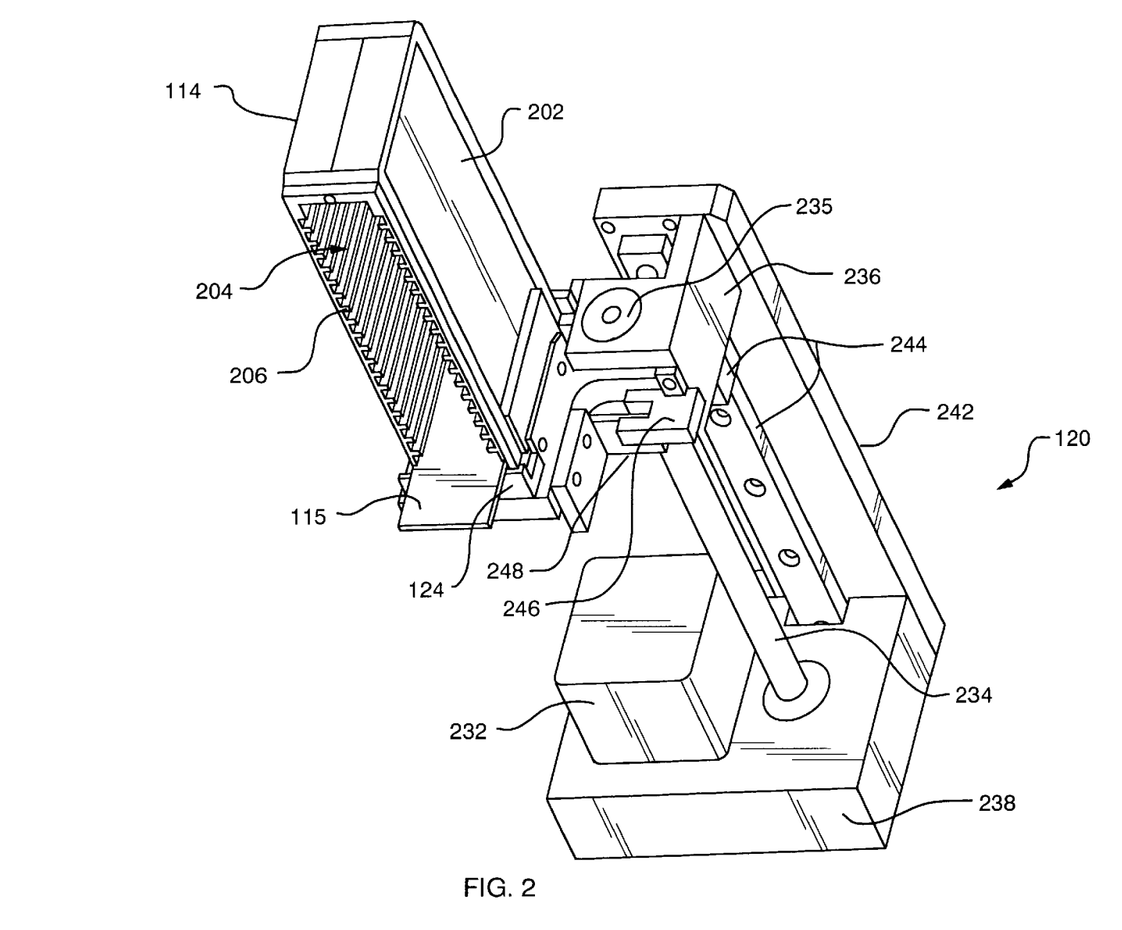
FIG. 2 is a slide storage cassette and an elevator in accordance with an embodiment of the invention.

FIG. 2 is a more detailed view of the slide storage cassette 114 and the elevator 120 shown in FIG. 1. The cassette 114 comprises a body 202 having a chamber 204 that has a plurality of horizontal grooves 206. The opposing grooves 206 form individual compartments to retain the slides 115. Specifically, the grooves 206 support and contact the slides 115 along the longitudinal peripheries of the sides. The contact avoids the sample area of the slide 115. The spacing between the grooves is selected to allow individual slides 115 to be captured laterally by the slide feeder 116.

Within each compartment, there is spring (not shown) to retain the slide by friction. Each spring prevents the individual slides from falling out of the cassette 114. However, the spring retention force should be applied as not to cause the slide feeder 116 to have trouble extracting the individual slides.

It is desirable to structure the cassette 114 such that both ends of the slide 115 protrude from the cassette 116. The protruding end of the slide 115 away from the slide feeder 116 provides easy manual access without risk of finger contamination to the sample portion of the slide 115.

The elevator 120 comprises a motor 232, a leadscrew 234, and a carriage 236 mounted on a base 238. The cassette 116 attaches to the carriage 236. Although not shown in the drawing, the elevator base 238 houses a toothed timing belt and pulleys that connect the motor shaft to the leadscrew.

When actuated, the motor 232 rotates the leadscrew 234 which engages a leadscrew nut 235 in the carriage 236 and causes the cassette 114 to move up and down moving with the carriage 236. An arm 242, attached to the base 238, supports a linear bearing 242 which guides the motion of the carriage 236. The motor 232 is preferably a stepper motor.

Figure 3:
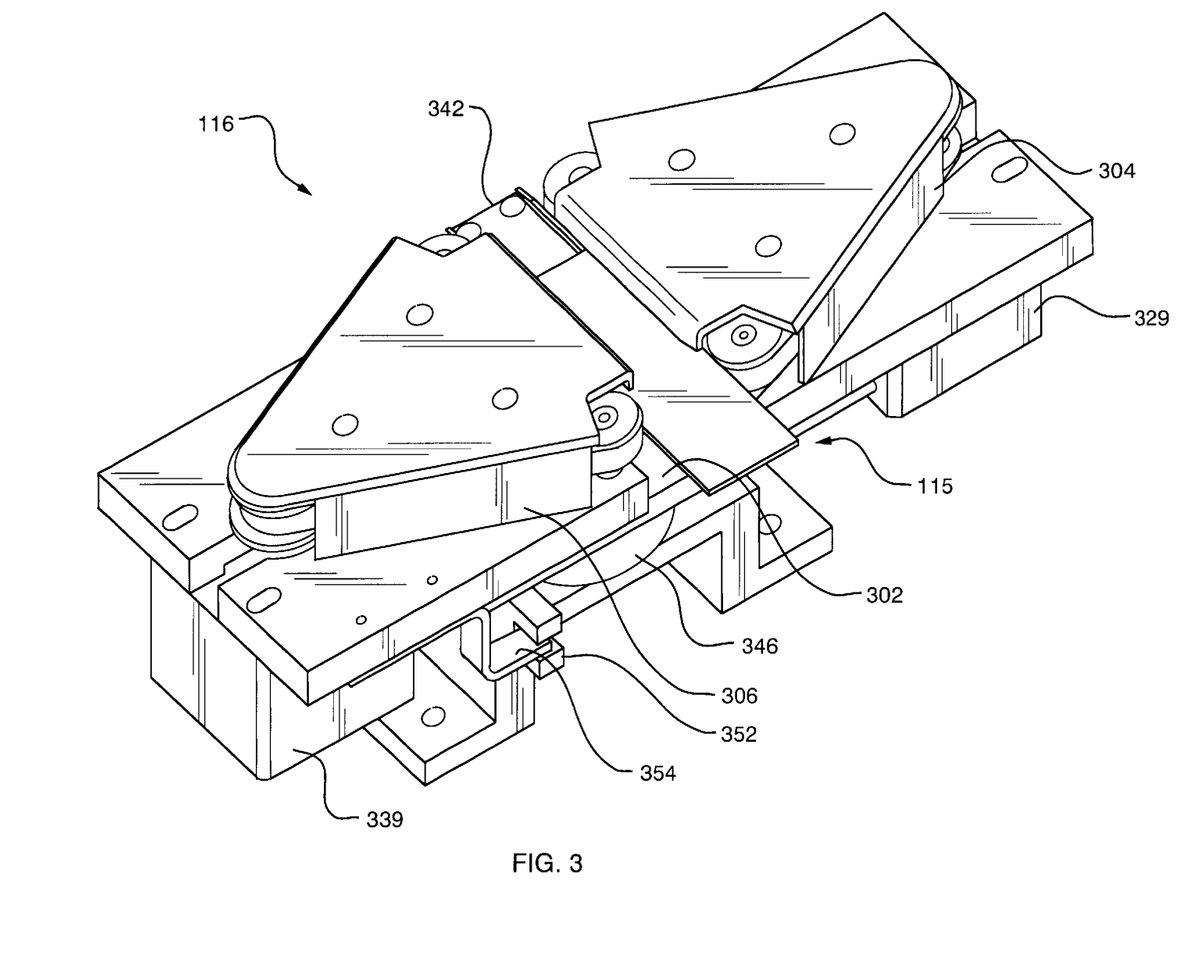
FIG. 3 is a top view of a slide feeder in accordance with an embodiment of the invention.
Figure 4:
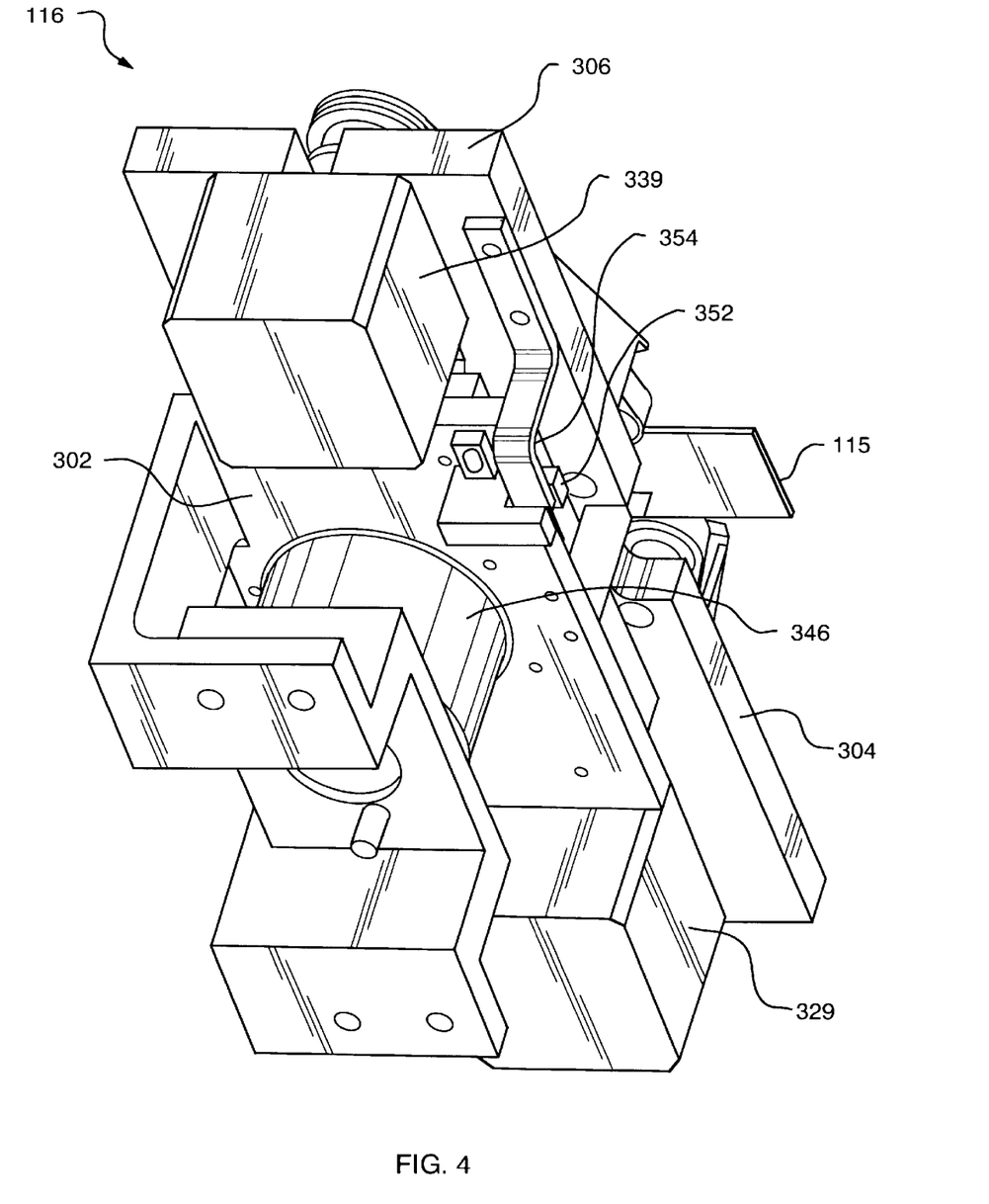
FIG. 4 is a bottom view of the slide feeder shown in FIG. 3.

It is desirable to calibrate the motor 232 to position the slides at the correct position for lateral grip by the slide feeder 116. This may be performed by an interrupt sensor 246 located on is the carriage 236 and sensor flag 248 located on the arm 242. As the sensor flag 248 passes through the sensor 246, a signal is sent to a motor controller (not shown) that energized the motor. The interruption point is the calibrating point by which all subsequent carriage positions are controlled as relative positions FIG. 3 and FIG. 4 are a top view and a bottom view of the slide feeder 116, respectively. The slide feeder 116 comprises a feeder base 302 having on its top surface two movable belt feed assemblies 304, 306. Between the two assemblies 304, 306, there is a guide track 342 that guides the slide 115. It is preferable that the guide track 342 be generally resistant to the abrasion caused by the motion of the slide 115. For example, it may be made of chrome-plated steel or hard stainless steel. Each assembly 304, 306 is powered by a motor 329, 339. A solenoid 346 is mounted at the base 302 and, when actuated, it causes the two assemblies 304, 306, supported on linear bearings 362, to close towards the guide track 342 and engage the slide 115.

The slide feeder 116 further comprises a interrupt sensor 352 and a sensor flag 354 attached to the base 302 and one of the assemblies 304, 306, respectively, to detect a closed or open position of assemblies 304, 306.

Figure 5:
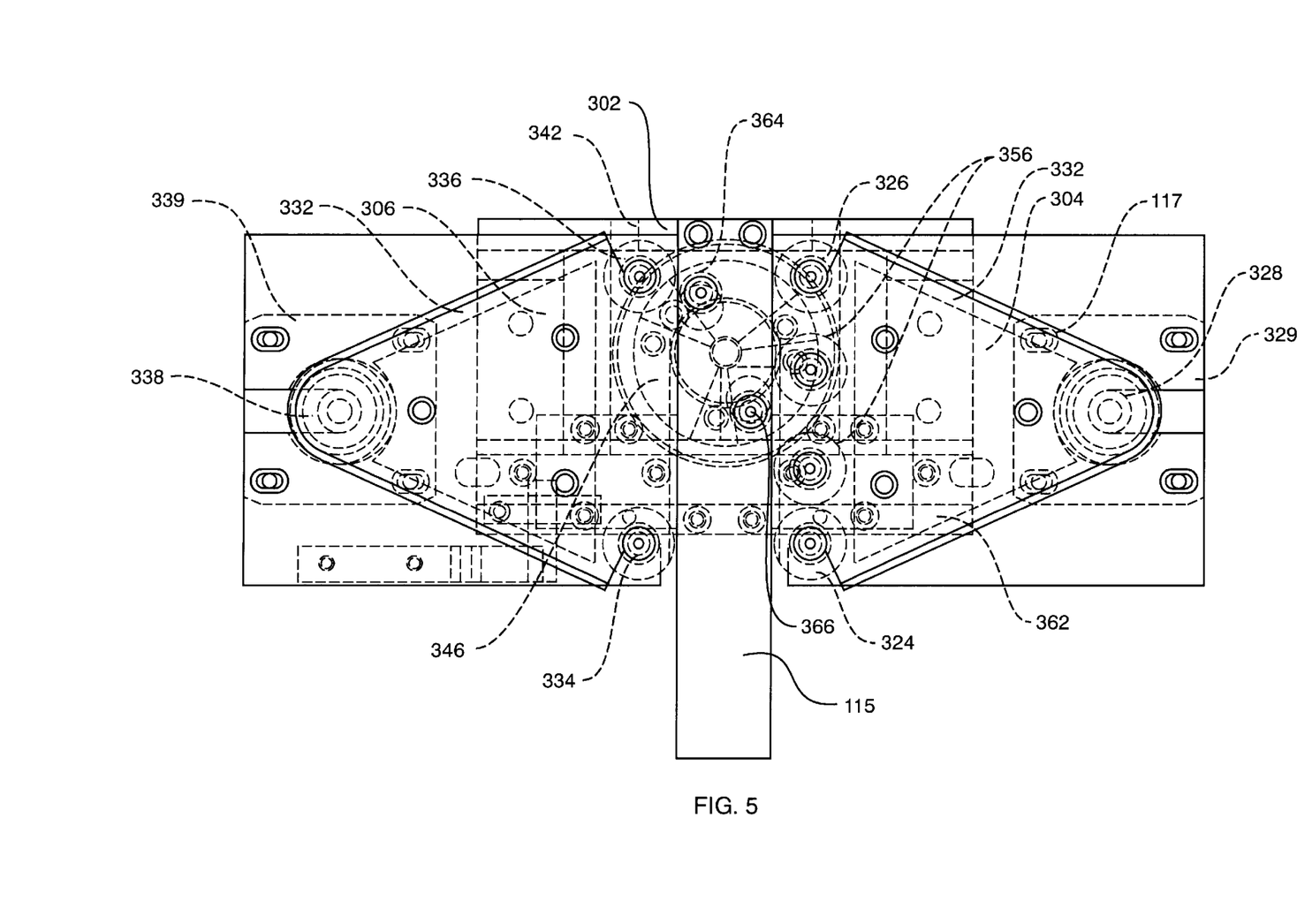
FIG. 5 is a hidden-line detail of the top view of the slide feeder shown in FIG. 3.

As shown in FIG. 5 each belt feed assembly 304, 306 comprises a belt 322, 332 held in place by three pulleys 324, 326, 328, 334, 336, 338. The belts 322, 332 are toothed elastomer belts that grip an end of the slide 115 and retain the slide as it travels through the slide feeder 116. The tooth 117 of the belts are bendable and the belts adapt to the width of the slide 115. Each motor 329, 339, when actuated, uses one of the pulleys 328, 338 to rotate the belts 322, 332.

The solenoid 346 is located approximately at midpoint of the feeder base 302. The solenoid has two pins 364, 366 which are located at opposing points with respect to the center of the solenoid. Each pin 364, 366 corresponds to a cam surface (not shown) located in an assembly 304, 306. When the solenoid 346 is actuated, the solenoid rotates and thus brings the pins 364, 366 into engagement with their corresponding cam surfaces and draw the two assemblies 304, 306 toward the guide track 342. Conversely, when the solenoid 346 is de-actuated, spring forces separate the movable belt feed assemblies 304, 306 from the guide track 346.

In the closed state, the belts 322, 332 grip the slide 115 and draw the slide 115 into the guide track 342. Continued movement of the belts propels the slide 115 to the sample holder 118 (FIG. 1). Idler pulleys 356 are positioned behind each belt 322, 332 to support the back side of the belt. This allows the belts 322, 332 to apply a constant and steady traction force to the slide 115 as it is propelled through the guide track 342 regardless of the position of the slide 115 along the guide track.

Figure 6:
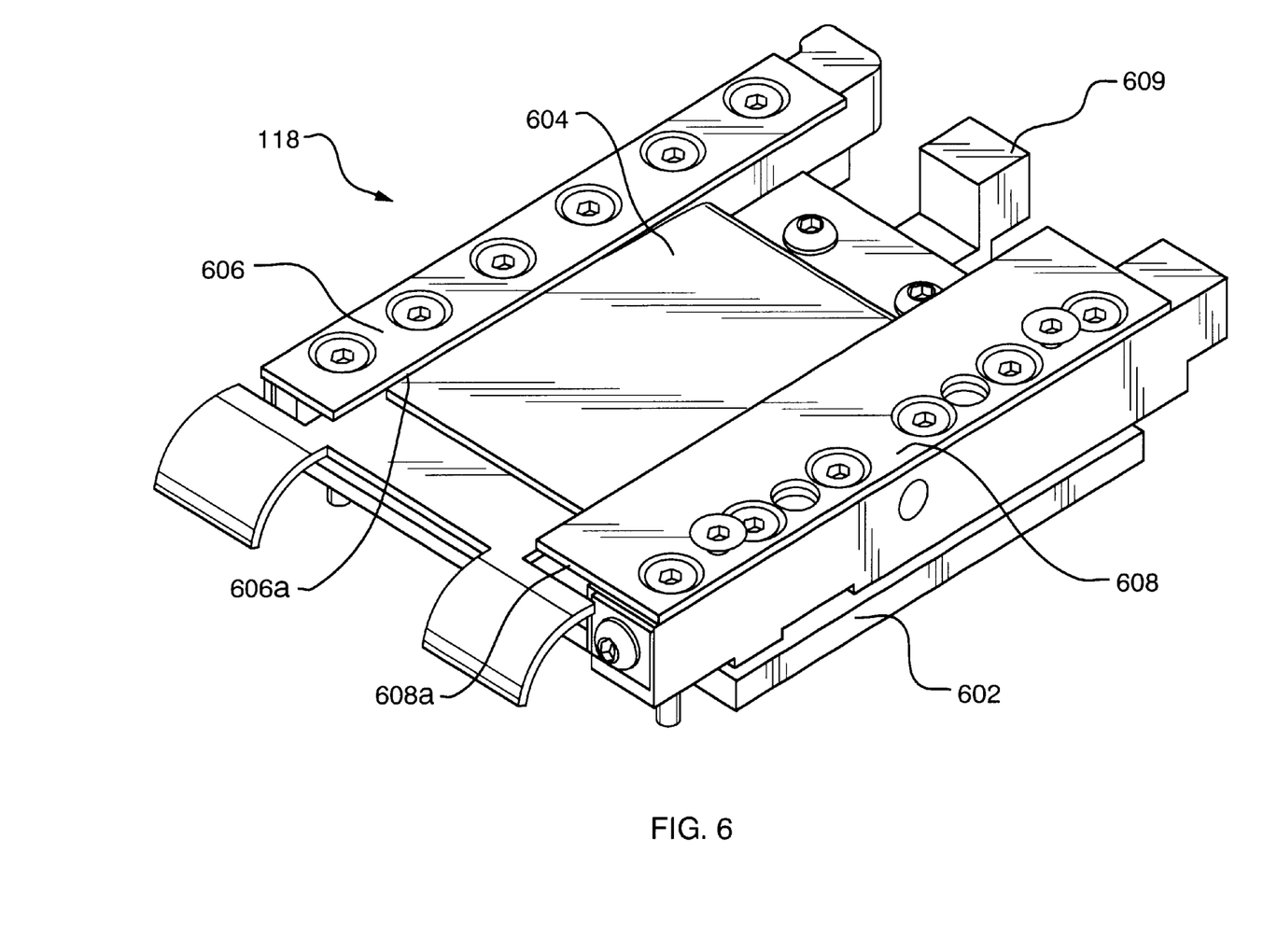
FIG. 6 is a sample holder in accordance with an embodiment of the invention.

As shown in FIG. 6, the sample holder 118 comprises retainer brackets 606, 608 mounted on a base 602. The base 602 also supports a spring loaded platform 604. The brackets 606, 608 adapted to position each slide along a longitudinal edge. Specifically, the bracket 606 is spring loaded toward the bracket 608, which is fixed in position. The platform 604 has a ramped portion adapted to receive the slides 115 emerging from the slide feeder 116.

Accordingly, as a slide enters the sample holder, it passes between the platform 604 and the horizontal surfaces 606a and 608a of the brackets and continues to move until it reaches a precision stop 609. The platform 604 positions the slide against the surfaces 606a and 608a, and the spring loaded bracket 606 position the slide laterally against a precision surface (not shown) in the bracket 608. When the slide reaches the stop 609, the motors stall, thereby preventing damage to the slide or the belts. A position sensor (not shown) can provide a signal to stop the belt movement after the slide is fully positioned.

Once the functions to be performed on the slide 115 are completed, a reverse operation of the loading operation is performed. The solenoid 346 is actuated and the belts 322, 332 rotate in a reverse direction to propel the slide 115 towards the cassette 114 and insert into a compartment of the cassette. Once the slide 115 is thus inserted, the solenoid 346 is de-actuated to release the grip on the slide 115. The elevator 120 then operates to align another slide with the slide feeder 116 to repeat the process.

The belts 322, 332 may be made of carbon impregnated urethane or other elastomer to allow for the dissipation of static charges. Conductive paths to dissipate charges from pulleys, the guide track and the slides themselves can be implemented with static-dissipation brushes and the use of electrically conductive materials.

What is claimed is:

1. An apparatus comprising:

a slide cassette to receive at least one slide and in a manner such that an end of the slide protrudes from the slide cassette;

a sample holder to retain the slide; and a slide feeder having grippers to grip the protruding end of the slide and to move the slide between the slide cassette and the sample holder.

2. The apparatus as in claim 1, wherein the slide passes through the slide feeder.

3. The apparatus as in claim 1, further comprising:

an elevator to receive the slide cassette, wherein the elevator moves the slide cassette until a selected slide in the slide cassette aligns with the slide feeder.

4. The apparatus as in claim 1, wherein the slide cassette further comprises:

a body having a chamber, in which the chamber has two opposing walls and at least one opening;

a plurality of grooves formed on the two opposing walls of the chamber, the grooves forming a compartment to receive the slide through the opening of the chamber.

5. The apparatus as in claim 4, wherein the slide cassette further comprises two openings in the chamber such that each end of the received slide protrudes from one of the openings in the chamber.

6. The apparatus as in claim 3, wherein the elevator further comprises a latch to latch the slide cassette to the elevator.

7. The apparatus as in claim 3, wherein the elevator comprises:

an motor; and an carriage, wherein the motor positions the carriage such that the selected slide in the slide cassette aligns with the slide feeder.

8. The apparatus as in claim 7, further comprising a first sensor to calibrate the motor.

9. The apparatus as in claim 1, wherein the slide feeder further comprises:

a first motor and a second motor, the first and second motors operating synchronously and having a first mode and a second mode;

a first belt and a second belt, the first and second belts spaced apart, the first belt powered by the first motor and the second belt powered by the second motor, wherein in the first mode, the first belt and second belt rotate in a forward direction to grip and transport the slide from the slide cassette to the sample holder, and in the second mode, the first and second belt rotate in a reverse direction to grip and transport the slide from the sample holder to the slide cassette.

10. The apparatus as in claim 9, further comprising:

a solenoid, wherein when the solenoid is actuateded, the solenoid closes the first belt and second belt in a manner to facilitate the first belt and the second belt to grip and propel the slide, and when the solenoid is de-actuated, the first belt and second belt retreat from the slide.

11. The apparatus as in claim 9, further comprising at least one pulley positioned behind at least one of the first belt and second belt.

12. The apparatus as in claim 10, further comprising:

a second sensor to sense a position of the first belt and second belt.

13. The apparatus as in claim 9, wherein the first belt and second belt are bendable toothed belts.

14. The apparatus in claim 9, wherein the first belt and the second belt are made of carbon impregnated elastomer to dissipate static charges.

15. The apparatus as in claim 1, wherein the sample holder further comprises;

a retainer having brackets retain the slide by longitudinal edges of the slide; and a platform having a ramped portion to receive the slide and a springed body portion to force the slide towards the brackets.

16. The apparatus as in claim 15, wherein each bracket of the retainer has a precision reference surface to seat the slide.

17. The apparatus as in claim 16, wherein at least one bracket has a spring to force the slide to the precision reference surface located on the other bracket.

18. The apparatus as in claim 15, wherein the retainer further comprising a precision stop to stop the slide at a predetermined point in the retainer.

19. A method for operating a microarray system comprising:

loading the slides in a manner such that an end of the slides protrude from a slide storage;

gripping the end of one of the protruding slides with grippers located at a slide feeder;

transferring the slide to a sample holder; and retaining the slide in the sample holder.

20. The method as in claim 19, further comprising;

performing one or more functions on the retained slide; and returning the slide to the slide storage.

21. The method as in claim 19, further comprising:

attaching the slide storage to the system before an operation of the system; and detaching the slide storage from the system after the operation of the system.

22. The method as in claim 19, further comprising;

moving the slide storage until a selected slide is in alignment with the grippers of the slide feeder.

23. The method as in claim 19, further comprising;

gripping the end of the selected slide; and transporting the slide through the slide feeder.

24. The method as in claim 19, further comprising;

loading the slides in a manner such that two ends of the slide protrude from the slide storage.

25. The method as in claim 22, further comprising;

calibrating the positioning of the slide storage.

26. The method as in claim 20, wherein the slide feeder has two modes, the method comprising:

in the first mode, the slide feeder transporting the slide from the slide storage to the sample holder; and in the second mode, the slide feeder transporting the slide from the sample holder to the slide storage.

27. The method as in claim 19, further comprising;

providing precision surfaces on brackets located at the sample holder;

providing at least one spring at the sample holder to guide the slide to the precision surfaces.

28. The method as in claim 19, further comprising;

providing a precision stop at the sample holder.

29. The method as in claim 28, further comprising:

causing the grippers to stop when the slide encounters the precision stop.

30. The method as in claim 19, wherein the grippers are a plurality of belts, the method further comprising:

forming bendable teeth on the belts.

31. A microarray system comprising:

an instrument for performing one or more functions on a slide;

a slide storage cassette to receive at least one slide and in a manner such that an end of the slide protrudes from the slide storage cassette;

a sample holder to retain the slide; and a slide feeder having grippers to grip the protruding end of the slide and reciprocate between the slide storage cassette and the sample holder.

32. The system as in claim 31, further comprising:

an elevator to receive the slide storage cassette, wherein the elevator moves the slide storage cassette until a selected slide in the slide storage cassette aligns with the slide feeder.

33. An apparatus for use in a microarray system that manipulates slides having sides and ends, the apparatus comprising:

a slide cassette to receive a plurality of slides, the slide cassette supporting each slide with an end of the slide protruding from the slide cassette;

a sample holder to retain a selected slide while the slide is being examined; and a slide feeder having grippers to grip the sides of the selected slide, the gripper gripping the sides of the protruding end of the slide to transport the slide from the slide cassette to the sample holder.

34. The apparatus of claim 33 wherein the slide feeder further grips the sides of the selected slide to transport the slide from the sample holder to the slide cassette.

35. The apparatus of claim 33 further including an elevator for positioning the cassette to align the selected slide with the grippers of the slide feeder.

36. The apparatus of claim 34 wherein the grippers include a set of belts that are positioned to contact the sides of the selected slide, the belts rotating in a given direction to transport the slide to the sample holder and in an opposite direction to return the slide to the slide cassette.

37. The apparatus of claim 36 further including a solenoid that when actuated moves the set of belts toward the sides of the slide to grip the selected slide, and when the solenoid is de-actuated moves the set of belts away from the sides of the slide to release the slide.

38. The apparatus of claim 36, wherein the belts respectively include a first surface that comes in contact with the slide, the first surface of one or both belts including bendable teeth.

39. The apparatus of claim 38, wherein the belts are made of carbon impregnated elastomer to dissipate static charges.

40. The apparatus of claim 33, wherein the sample holder further includes:
   a retainer having brackets that retain the slide by the sides of the slide; and
   a platform having a ramped portion to receive the slide and a springed body portion to force the slide towards the brackets.

41. The apparatus of claim 40, wherein at least one bracket has a spring to force the slide into contact with the other bracket.

42. The apparatus of claim 41, wherein the retainer includes at one end a stop to prevent the slide from moving beyond a predetermined point in the retainer.

43. The apparatus of claim 33 wherein the slide cassette includes:
   a body having a chamber, in which the chamber has two opposing walls and a first opening; and
   a plurality of grooves formed on the two opposing walls of the chamber, each groove forming a compartment to receive a given slide through the opening of the chamber.

44. The apparatus of claim 43, wherein the slide cassette further includes a second opening in the chamber such that the two ends of the received slide protrude respectively from the two openings in the chamber, to allow the slides to be removed from or returned to the slide cassette from either side of the slide cassette.

45. The apparatus of claim 35, wherein
   the elevator includes a spring latch, and
   the slide cassette includes a protrusion that the latch cooperates with in order to hold the cassette in place on the elevator.

* * * * *